US011589935B2

(12) United States Patent
Doi

(10) Patent No.: US 11,589,935 B2
(45) Date of Patent: Feb. 28, 2023

(54) OPERATION DEVICE FOR SURGICAL MANIPULATOR AND ROBOTICALLY-ASSISTED SURGICAL SYSTEM

(71) Applicants: KAWASAKI JUKOGYO KABUSHIKI KAISHA, Kobe (JP); MEDICAROID CORPORATION, Kobe (JP)

(72) Inventor: Wataru Doi, Kashihara (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 601 days.

(21) Appl. No.: 16/724,537

(22) Filed: Dec. 23, 2019

(65) Prior Publication Data
US 2020/0205907 A1 Jul. 2, 2020

(30) Foreign Application Priority Data
Dec. 26, 2018 (JP) .............................. JP2018-243422

(51) Int. Cl.
*B25J 9/16* (2006.01)
*A61B 34/30* (2016.01)
(Continued)

(52) U.S. Cl.
CPC .............. *A61B 34/30* (2016.02); *A61B 34/71* (2016.02); *A61B 90/06* (2016.02); *B25J 9/102* (2013.01);
(Continued)

(58) Field of Classification Search
CPC ........ B25J 9/102; B25J 13/02; B25J 17/0283; B25J 9/1689; B25J 19/0016; B25J 13/00;
(Continued)

(56) References Cited

U.S. PATENT DOCUMENTS 11,397,421 B2 * 7/2022 Cella ................ G05B 19/41865
11,397,422 B2 * 7/2022 Cella ........................ H04L 1/18
(Continued)

FOREIGN PATENT DOCUMENTS

JP   H05-20882 U    3/1993
JP   H11-333764 A   12/1999
(Continued)

OTHER PUBLICATIONS

Shan et al., An articulated universal joint based flexible access robot for minimally invasive surgery, 2011, IEEE, pg. (Year: 2011).*
(Continued)

*Primary Examiner* — McDieunel Marc
(74) *Attorney, Agent, or Firm* — Oliff PLC

(57) ABSTRACT

An operation device for a surgical manipulator includes an input device that operates the surgical manipulator. The input device includes a plurality of joints and a plurality of motors that drives the plurality of joints, and reduction ratios in power transmission paths from the plurality of motors to the plurality of joints, respectively, are 0.5 or more and 30 or less.

20 Claims, 10 Drawing Sheets

(51) Int. Cl.
*A61B 34/00* (2016.01)
*A61B 90/00* (2016.01)
*B25J 9/10* (2006.01)
*B25J 19/00* (2006.01)
*B25J 17/02* (2006.01)

(52) U.S. Cl.
CPC ......... *B25J 9/1689* (2013.01); *B25J 17/0283* (2013.01); *B25J 19/0016* (2013.01); *A61B 2034/301* (2016.02); *A61B 2034/306* (2016.02); *A61B 2090/067* (2016.02)

(58) Field of Classification Search
CPC ........ B25J 9/1633; B25J 13/085; B25J 9/009; A61B 34/37; A61B 34/71; A61B 90/06; A61B 34/30; A61B 34/74; A61B 2034/301; A61B 2090/067; A61B 2034/306; A61B 34/20; A61B 34/70; A61B 34/32; A61B 17/16; A61B 34/76; A61B 18/148; A61B 17/1626; A61B 2018/00565; A61B 2034/107; A61B 2018/00601; A61B 2090/066; A61B 2034/2046; G16H 40/63; G05B 2219/40191; G05B 2219/45117

See application file for complete search history.

(56) References Cited

U.S. PATENT DOCUMENTS

| | | | |
|---|---|---|---|
| 2014/0222207 A1* | 8/2014 | Bowling | A61B 34/10 |
| 2018/0021094 A1* | 1/2018 | Matsuda | A61B 34/30 |
| | | | 600/102 |
| 2021/0038336 A1* | 2/2021 | Ogata | A61B 34/77 |

FOREIGN PATENT DOCUMENTS

| | | |
|---|---|---|
| JP | 2008-541797 A | 11/2008 |
| JP | 2016-518878 A | 6/2016 |
| JP | 2017-104964 A | 6/2017 |
| WO | 2014/146090 A1 | 9/2014 |
| WO | 2016/119495 A1 | 8/2016 |

OTHER PUBLICATIONS

Gossenlin et al., Design of a High Fidelity Haptic Device for Telesurgery, 2005, IEEE, p. 205-210 (Year: 2005).*

Kim et al., A Teleoperated Minimally Invasive Surgical System with an Additional Degree of Freedom Manipulator, 2010, IEEE, p. 90-94 (Year: 2010).*

Yanagihara et al., Robotic Creation of Operating Space for Minimally Invasive Hip Joint Surgery, 2007, IEEE, p. 2648-2654 (Year: 2007).*

* cited by examiner

OPERATION DEVICE FOR SURGICAL MANIPULATOR AND ROBOTICALLY-ASSISTED SURGICAL SYSTEM

TECHNICAL FIELD

The present invention relates to an operation device for a surgical manipulator and a robotically-assisted surgical system.

BACKGROUND ART

Conventionally known, for example, in a master input device of a robot guide catheter system, is a technique of compensating a weight of a link of the input device by a motor (Japanese Translation of PCT International Application Publication No. JP-T-2008-541797 A (See, in particular, paragraph [0066])). In this technique, when an operator intends to manually operate a master input device, the master input device stays in an appropriate position.

SUMMARY OF INVENTION

Technical Problem

A surgical manipulator is known as a medical robot. An input device for the surgical manipulator may be required to be lightly movable by an operator. Meanwhile, a speed reducer is generally provided between a motor and a link of the input device. Therefore, when the above technique is simply applied to the surgical manipulator and the link of the input device is driven by the motor, the operator cannot move the input device lightly because of the speed reducer.

The present invention has been made to solve the above-described problem, and has an object to provide an operation device for a surgical manipulator including an input device that can be lightly moved by an operator, and a robotically-assisted surgical system.

Solution to Problem

The inventors have diligently studied measures for solving the above problem.

As a result, the following findings have been obtained.

That is, it has been found that an operator can lightly move an input device for a surgical manipulator including an arm unit, a wrist unit connected to a distal end of the arm unit, and an operation unit provided at a distal end of the wrist unit (hereinafter, the input device for a surgical manipulator may be simply referred to as an input device) when a reduction ratio is 0.5 or more and 30 or less. It has been also found that when the reduction ratio decreases, an operation distance required for the operation unit to move the surgical manipulator by a predetermined distance increases, but this causes no problem as long as the reduction rate is within the above range. In addition, the speed reducer, such as a reduction gear of the wrist unit can be smaller than the speed reducer, such as a reduction gear of the arm unit, and thus causes a lower drag due to friction. Therefore, it has been found that the reduction ratio at which the input device can be moved lightly may be larger in the wrist unit than in the arm unit. Further, it has been found that the reduction ratio is preferably 1 or more and 2 or less in the arm unit, and the reduction ratio is preferably 20 or more and 30 or less in the wrist unit.

Therefore, an operation device for a surgical manipulator according to an aspect of the present invention includes an input device and a controller, in which the input device includes an arm unit having one or more joints, and a wrist unit having one or more joints connected to a distal end of the arm unit, an operation unit provided at a distal end of the wrist unit and operated by an operator, a plurality of motors for respectively driving the one or more joints of the arm unit and the one or more joints of the wrist unit, and a plurality of rotation angle sensors for respectively detecting rotation angles of the plurality of motors or rotation angles of the joints, the controller is configured to control operations of the plurality of motors based on the rotation angles detected by the plurality of rotation angle sensors, and reduction ratios in power transmission paths from the plurality of motors to the plurality of joints, respectively, are 0.5 or more and 30 or less.

With this configuration, since the reduction ratios in the power transmission paths from the plurality of motors to the plurality of joints, respectively, are 0.5 or more and 30 or less, the operator can move the input device lightly.

The reduction ratio in the arm unit may be smaller than the reduction ratio in the wrist unit.

With this configuration, the reduction ratio of the arm unit, which has a higher drag due to friction of the speed reducer in comparison with the wrist unit, is smaller than the reduction ratio of the wrist unit, and the operator can thereby move the input device more lightly.

The reduction ratio in the arm unit may be 1 or more and 2 or less.

With this configuration, the reduction ratio in the arm unit is in a preferable range, and thus the operator can move the input device even more lightly.

The reduction ratio in the wrist unit may be 20 or more and 30 or less.

With this configuration, the reduction ratio in the wrist unit is in a preferable range, and thus the operator can move the input device even more lightly.

An auxiliary spring is further included that is provided in a predetermined joint of the one or more joints of the arm unit or the one or more joints of the wrist unit, and that generates a torque that cancels a part of a torque generated in the predetermined joint by a weight of the arm unit or the wrist unit. The controller may be configured to control the operations of the plurality of motors based on the rotation angles detected by the plurality of rotation angle sensors or the rotation angles and the torque generated by the auxiliary spring such that postures of the arm unit and the wrist unit do not change due to gravity.

This configuration can reduce a load on the motors driving the joints such that the postures of the arm unit and the wrist unit do not change due to gravity, and the motors to be downsized.

The arm unit may have three or four joints, and the wrist unit may have three joints.

With this configuration, degrees of freedom of the arm unit and the wrist unit are 6 or 7, and this improves operability of the input device.

The three joint axes of the three joints of the wrist unit may intersect at one point.

This configuration allows the three joints of the wrist unit to configure a gimbal mechanism, and the operation unit to move in any direction without changing the posture of the operation unit operated by the operator.

The controller may be configured, based on the rotation angles detected by the plurality of rotation angle sensors, i) calculate the position of the operation unit, ii) output the calculated position of the operation unit to a surgical manipulator, and iii) control the operation of the plurality of motors such that the postures of the arm unit and the wrist unit do not change due to gravity.

With this configuration, the controller controls the operations of the plurality of motors such that the postures of the arm unit and the wrist unit do not change due to gravity. The operation unit therefore stays at a position where the operator has stopped operating the operation unit.

In addition, a robotically-assisted surgical system according to an aspect of the present invention includes a surgical manipulator having a distal end to which a surgical tool is detachably attached, and a remote operation device including an input device and a controller that operate the surgical manipulator, in which the input device includes an arm unit having one or more joints, and a wrist unit having one or more joints connected to a distal end of the arm unit, an operation unit provided at a distal end of the wrist unit and operated by an operator, a plurality of motors for respectively driving the one or more joints of the arm unit and the one or more joints of the wrist unit, and a plurality of rotation angle sensors for respectively detecting rotation angles of the plurality of motors or rotation angles of the joints, the controller is configured to control operations of the plurality of motors based on the rotation angles detected by the plurality of rotation angle sensors, and reduction ratios in power transmission paths from the plurality of motors to the plurality of joints, respectively, are 0.5 or more and 30 or less.

This configuration allows the operator to lightly move the input device when the operator operates the surgical manipulator through the input device.

Advantageous Effects of Invention

The present invention produces an effect of providing an operation device for a surgical manipulator including an input device that an operator can move lightly, and a robotically-assisted surgical system.

DESCRIPTION OF EMBODIMENTS

Figure 1:
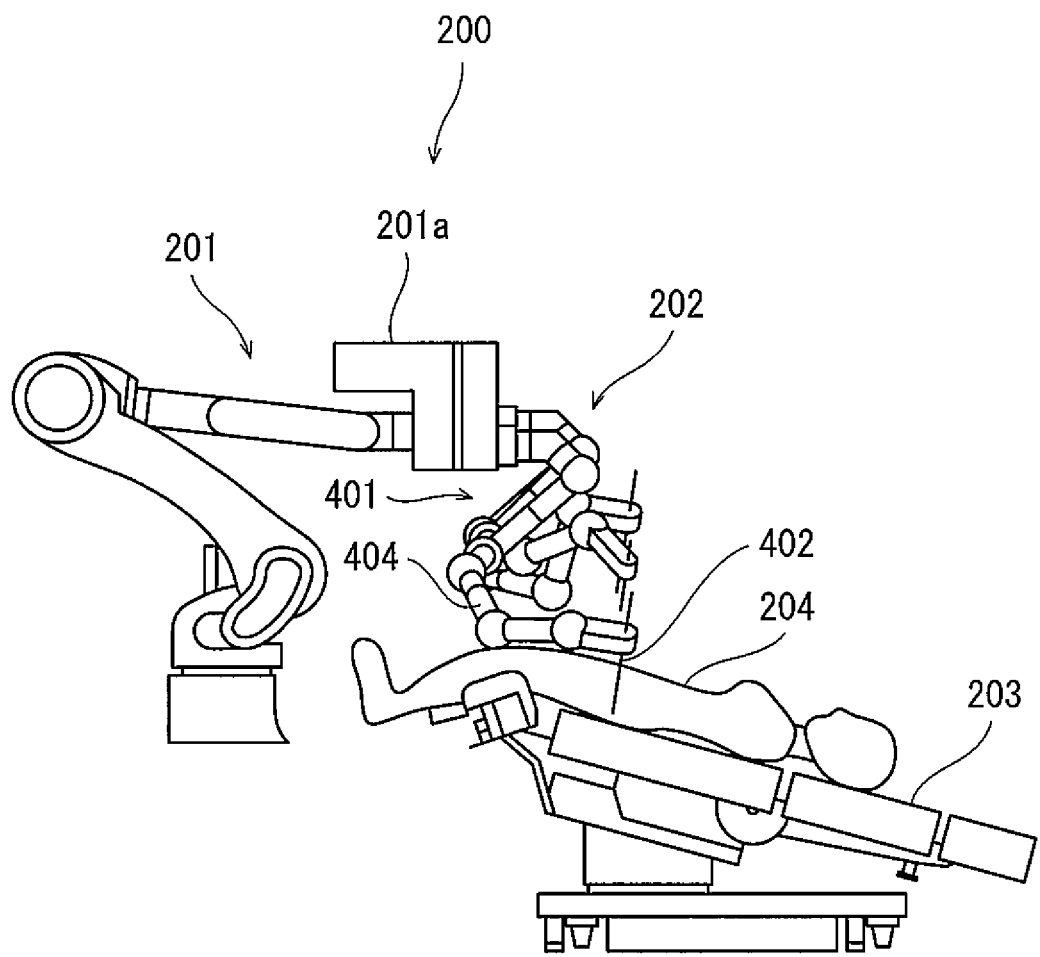
FIG. 1 is a schematic diagram showing an outline of an example of a robotically-assisted surgical system including a surgical manipulator according to Embodiment 1 of the present invention.

Embodiments of the present invention will now be described with reference to the drawings. In the following description, the same or corresponding elements are denoted by the same reference signs throughout all the drawings, and a redundant description thereof is omitted.

Note that the following drawings are drawings for describing the present invention, and therefore, in the drawings, in some cases, elements irrelevant to the present invention are omitted, dimensions are not accurate due to exaggeration or the like, or the corresponding elements in the drawings do not match.

Further, the present invention is not limited to the following embodiments.

Embodiment 1

[Configuration]
{Hardware Configuration}

Figure 2:
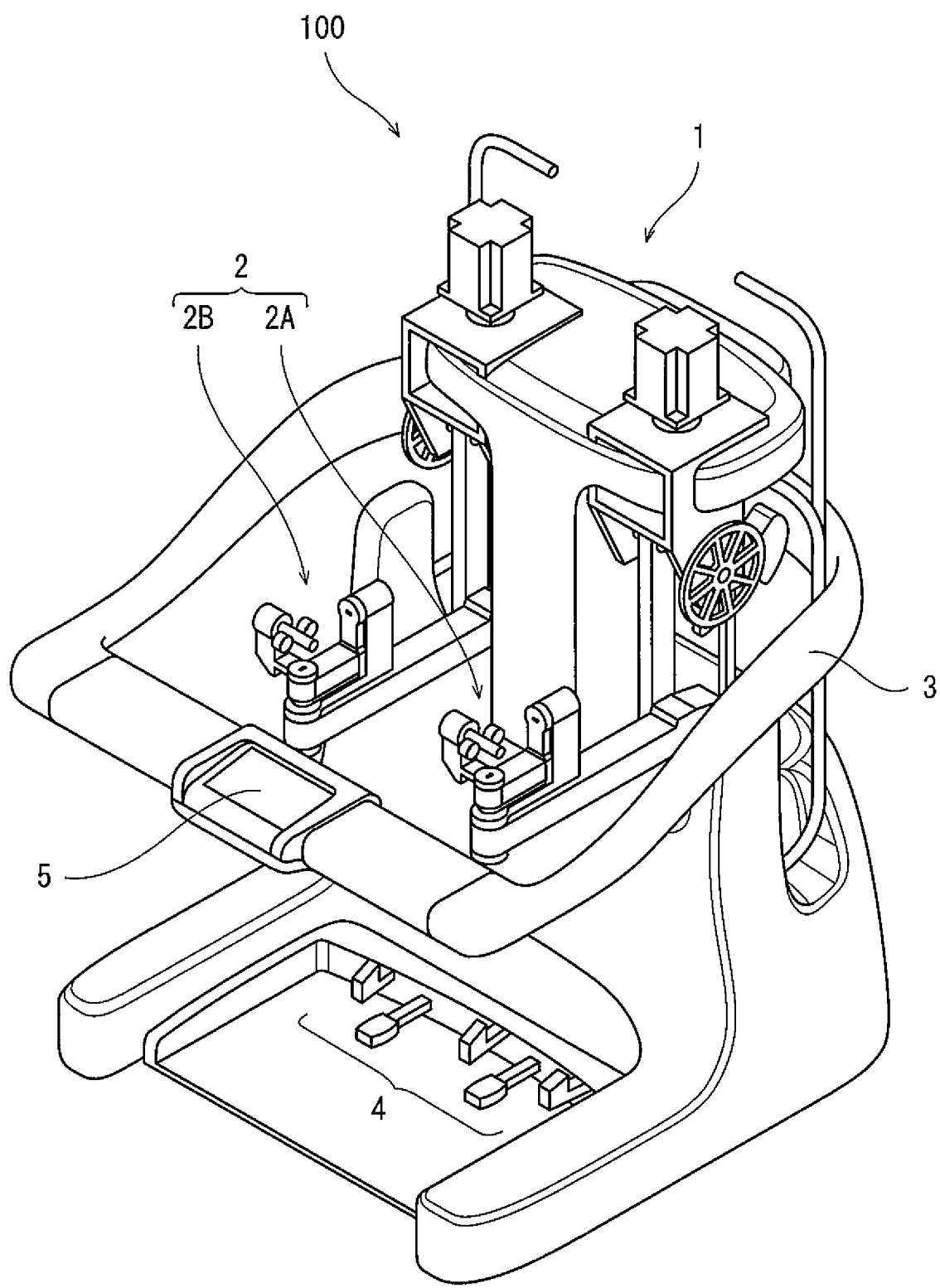
FIG. 2 is a schematic diagram showing an outline of an appearance of an example of a remote operation device included in the robotically-assisted surgical system in FIG. 1.

FIG. 1 is a schematic diagram showing an outline of an example of a robotically-assisted surgical system including a surgical manipulator according to Embodiment 1 of the present invention. FIG. 2 is a schematic diagram showing an outline of an appearance of an example of a remote operation device included in the robotically-assisted surgical system in FIG. 1. Hereinafter, descriptions will be made considering that the vertical direction in FIGS. 1 and 2 are the vertical direction in a use environment (use space) of the robotically-assisted surgical system.

Referring to FIGS. 1 and 2, a robotically-assisted surgical (RAS) system 200 includes a positioner 201, a surgical manipulator 202, and a remote operation device 100.

<Robotically-Assisted Surgical System 200>

Referring to FIG. 1, for example, an operating table 203 is disposed in an operating room, and a patient 204 is laid on the operating table 203. The positioner 201 is disposed near the operating table 203. The positioner 201 is placed on an appropriate table (not shown). The positioner 201 is configured by, for example, an articulated robot. A base 201a is provided at a distal end of the positioner 201. A surgical manipulator 202 configured by an articulated robot is attached to the base 201a. The surgical manipulator 202 has, for example, a base part, an arm 401, and an end effector that is detachably attached to the arm 401. The base part is fixed to the base 201a, and the base part and a link 404, and links 404 are connected by a plurality of joints. A plurality of (here, for example, four) arms 401 is connected to the base part. A surgical tool 402 is attached to a distal end of each of the plurality of arms 401 as an end effector. The surgical tool 402 includes, for example, forceps and an endoscope.

The positioner 201 transports the surgical manipulator 202 to a position where the surgical manipulator 202 is suitable for performing an operation on the patient 204. Then, the positioner 201 holds the base 201a in a horizontal state. Note that the base 201a may be inclined from the horizontal state.

<Remote Operation Device 100>

FIG. 2 shows an outline of the remote operation device 100. FIG. 2 is a diagram to help understand a concept of the remote operation device 100. Thus, FIG. 2 shows, in particular, a detailed structure of the input device 2 differently from a specific structure of the input device 2 to be described later, shown in FIGS. 3 to 8.

Referring to FIG. 2, the remote operation device 100 is a device with which an operator (a doctor who performs a surgical operation) controls an operation of the surgical manipulator 202 to perform a surgical operation. The remote operation device 100 is electrically connected to the positioner 201 and the surgical manipulator 202 by wire or wirelessly. The remote operation device 100 is disposed, for example, near the operating table or in a separate room.

Here, the remote operation device 100 includes a body 1, the input device 2, a plurality of pedals 4, a display unit 5, and a viewer (not shown).

The body 1 is formed in a substantially L shape as viewed from a side. A right input device 2A and a left input device 2B are provided on a right side and a left side of the body 1, respectively, as facing to the body 1. The right input device 2A and the left input device 2B are used for the operator to operate with the right and left hands, respectively. The right input device 2A and the left input device 2B function as master input devices for the arms 401 of the surgical manipulator 202 as a slave robot.

A U-shaped support member 3 is provided in an upper part of the body 1 so as to protrude forward. The display unit 5 is provided at a center of a front end of the support member 3. The display unit 5 is configured by, for example, a touch panel, and functions as a screen on which the operator inputs information for performing various settings on the remote operation device 100, or as a screen which displays the information. The viewer (not shown) is provided in an upper part of the remote operation device 100. However, since a configuration and a function of the viewer are well known, the viewer is not shown in FIG. 2 to make the input device 2 easy to see. The viewer displays an image captured by an endoscope (surgical tool 402) attached as the end effector to the distal end of one of the arms 401 of the surgical manipulator 202.

The plurality of (four, here) pedals 4 are provided at a lower part of the body 1 so as to protrude forward. The plurality of pedals 4 switches a connection between the right input device 2A and the left input device 2B and the arms of the surgical manipulator 202, zooms an image displayed on a monitor 5, and the like.

The operator, for example, operates the right input device 2A and the left input device 2B with the right hand and the left hand, respectively, to perform an operation while sitting on a chair disposed in front of the remote operation device 100, and viewing an image of the body of the patient 204 displayed on the viewer.

<Input Device 2>

Figure 3:
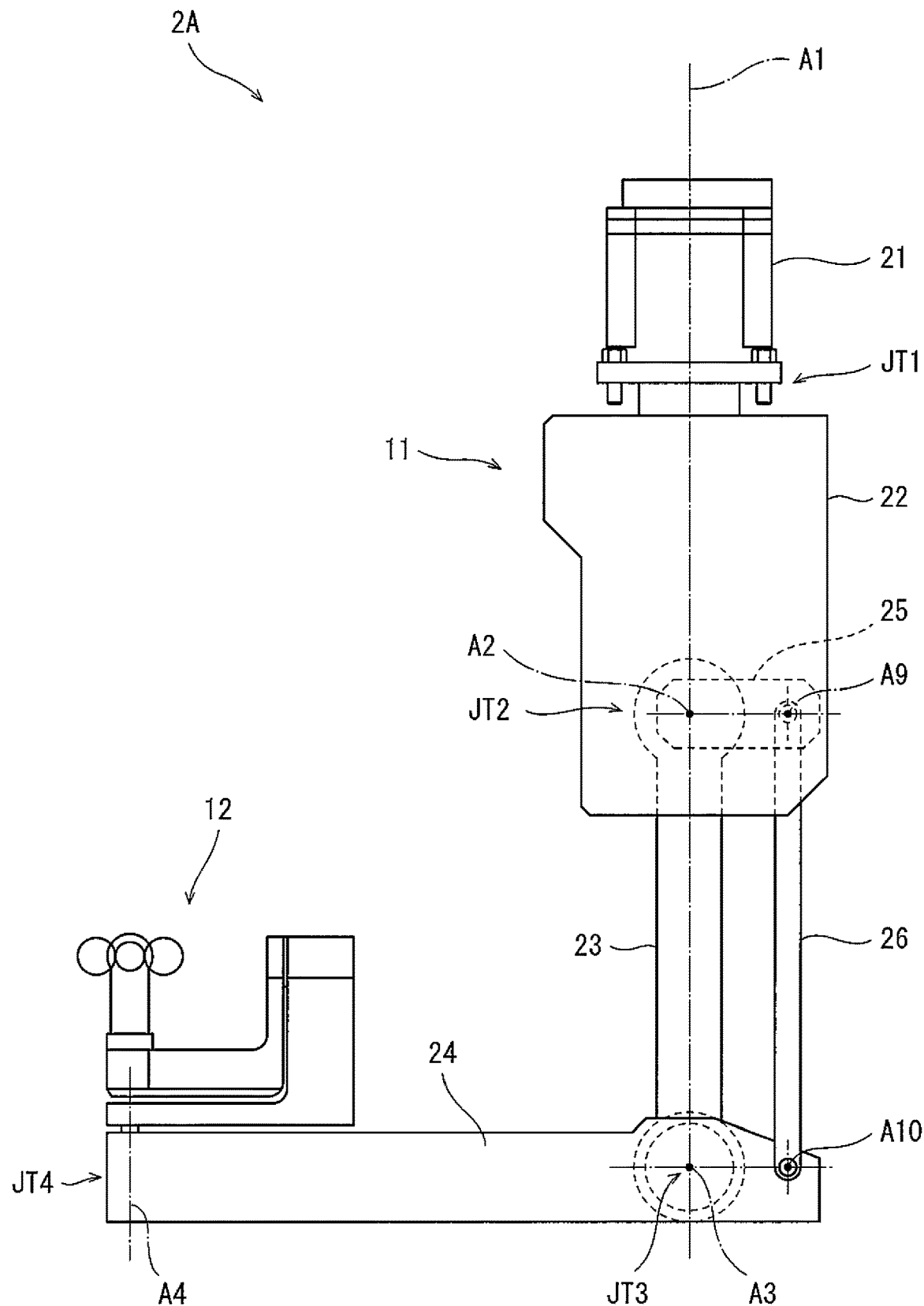
FIG. 3 is a side view schematically showing an outline of an input device of the remote operation device in FIG. 2.

FIG. 3 is a side view schematically showing an outline of the input device 2 shown in FIG. 2. FIG. 3 shows a simplified configuration of the input device 2. Refer to FIGS. 4 to 8 for an example of a specific structure of the input device 2. FIG. 3 shows the right input device 2A. The left input device 2B has a structure in which the left and right direction is simply in reverse to the left and right direction of the structure of the right input device 2A. Therefore, a description of the left input device 2B is omitted. Hereinafter, for convenience, the up and down direction and the left and right direction in FIG. 3 are the up and down direction and the front and rear direction of the right input device 2A, respectively. The right input device 2A takes a reference posture shown in FIG. 3 in an initial state.

Referring to FIG. 3, the right input device 2A takes a substantially L-shaped reference posture as viewed from a side. Hereinafter, the reference posture of the right input device 2A may be simply referred to as "reference posture". The right input device 2A includes an arm unit 11 and a wrist unit 12. In the claims and the specification, rotation axes A1 to A7 of joints JT1 to JT7 may be referred to as "joint axes".

{Arm Unit 11}

The arm unit 11 includes, for example, a base body 21, a first link 22, a second link 23, and a third link 24. The base body 21 is fixed to the body 1 of the remote operation device 100. One end (here, upper end) of the first link 22 is connected via a first joint JT1 to one end (here, lower end) of the base body 21 in the up and down direction rotatably around a first rotation axis A1 extending in the up and down direction. One end (here, upper end) of the second link 23 is connected via a second joint JT2 to the other end (here, lower end) of the first link 22 rotatably around a second rotation axis A2 orthogonal to the first rotation axis A1 and extending in the left and right direction. One end (rear end in the reference posture) of the third link 24 is connected via a third joint JT3 to the other end (here, lower end) of the second link 23 rotatably around a third rotation axis A3 extending in parallel to the second rotation axis A2. One end of a swing member 25 is provided at the other end of the first link 22 rotatably around the second rotation axis A2. One end (here, upper end) of an auxiliary link 26 is connected to the other end of the swing member 25 rotatably around a ninth rotation axis A9. The ninth rotation axis A9 extends in parallel to the second rotation axis A2 and apart from the second rotation axis by a predetermined distance. The other end (here, lower end) of the auxiliary link 26 is connected to one end of the third link rotatably around a tenth rotation axis A10. The tenth rotation axis A10 extends in a direction parallel to the third rotation axis A3 and apart from the third rotation axis, toward the one end of the third link 24 from the third rotation axis, by the predetermined distance. That is, the auxiliary link 26 and the second link 23 configure parallel links.

The wrist unit 12 is connected via a fourth joint JT4 to the other end (front end in the reference posture) of the third link 24 rotatably around a fourth rotation axis A4. The fourth rotation axis A4 extends so as to be orthogonal to a plane including the third rotation axis A3 and the tenth rotation axis A10.

Figure 4:
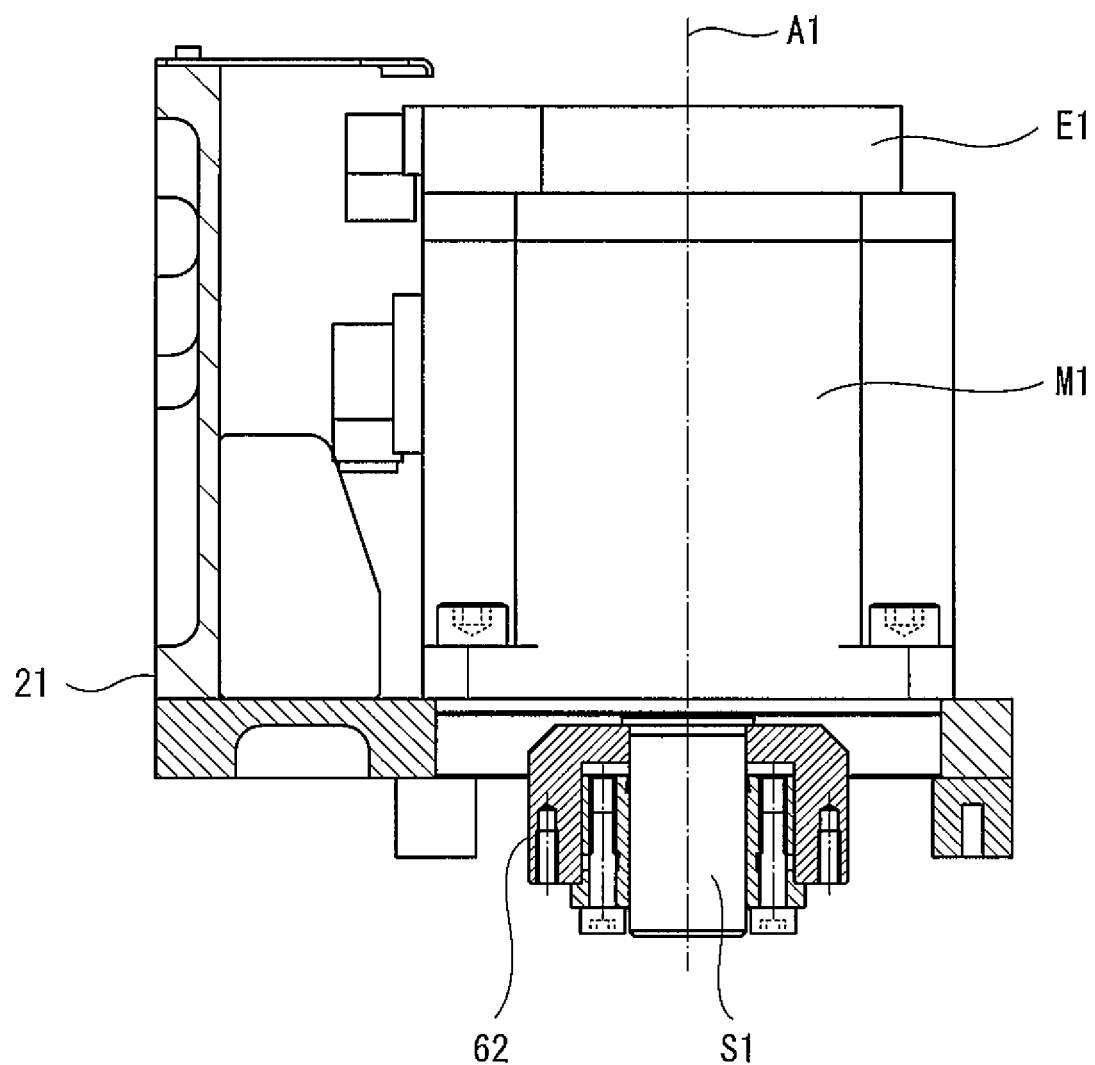
FIG. 4 is a cross-sectional view showing a vertical cross section of a shoulder unit of an arm unit of the input device in FIG. 3.

FIG. 4 is a cross-sectional view showing a vertical cross section of a shoulder unit of the arm unit 11 of the input device in FIG. 3. Referring to FIG. 4, the shoulder unit is configured by a base body 21, which is formed in a frame shape. The base body 21 is provided with a first motor M1 facing downward. Specifically, the first motor M1 is provided such that a main shaft S1 is coaxial with the first rotation axis A1. The first motor M1 is provided with a first rotation angle sensor E1 that detects a rotation angle of the first motor M1. The first rotation angle sensor E1 only needs to be able to detect the rotation angle, and is configured by, for example, an encoder or a tachometer. The "rotation angle sensor" may be provided at the joint to detect the rotation angle of the joint. This also applies to second to seventh rotation angle sensors E2 to E7 to be described later. Here, the first rotation angle sensor E1 is configured by an encoder directly connected to the main shaft S1 of the first motor M1. The main shaft S1 is butt-connected coaxially to a first rotation shaft R1 (see FIG. 5) of the first link 22 by a cylindrical connection member 62. Specifically, the main shaft S1 of the first motor M1 and the first rotation shaft R1 are connected such that both end surfaces thereof are butt-joined.

Figure 5:
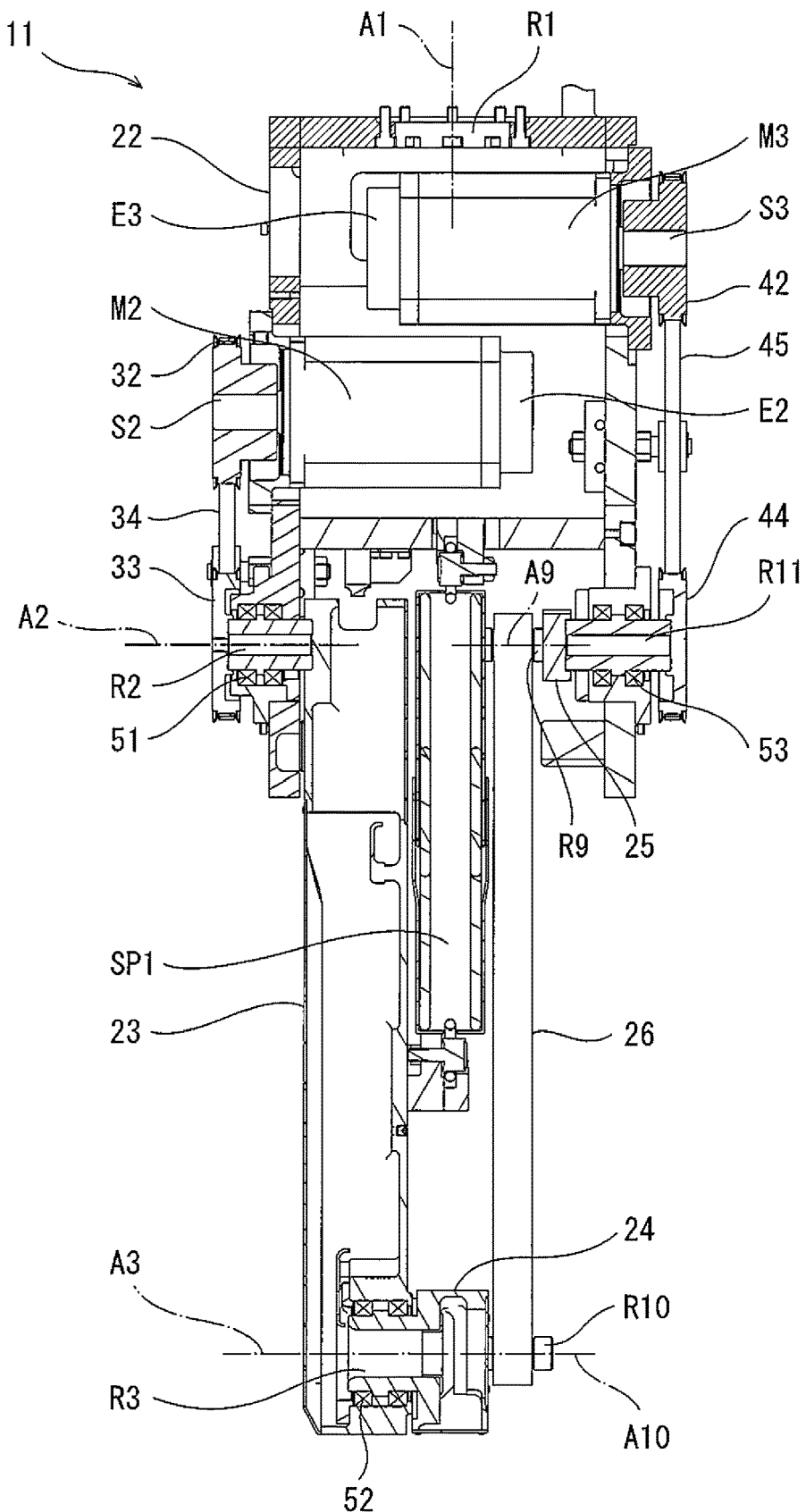
FIG. 5 is a cross-sectional view showing a vertical cross section of an upper arm unit of the arm unit of the input device in FIG. 3.

FIG. 5 is a cross-sectional view showing a vertical cross section of an upper arm unit of the arm unit 11 of the right input device 2A in FIG. 3. Referring to FIG. 5, the upper arm unit of the arm unit 11 includes the first link 22, the second link 23, and the auxiliary link 26. The first link 22 is formed in a frame shape. The first rotation shaft R1 is provided at the one end (here, upper end) of the first link 22. As described above, the first rotation shaft R1 is coaxially connected to the main shaft S1 of the first motor M1. The first joint JT1 is configured by the first rotation shaft R1 and the first motor M1. As a result, the first link 22 can freely rotate around the first rotation axis A1 with respect to the base body 21. The rotation angle of the first motor M1 created by the rotation of the first link 22 can be detected by the first rotation angle sensor E1. The first rotation shaft R1 can be rotationally driven by the first motor M1.

The second link is formed in a hollow rod shape. A second rotation shaft R2 is provided at the one end (upper end) of the second link 23. The second rotation shaft R2 is attached to the other end (lower end) of the first link 22 via a bearing 51 rotatably around the second rotation axis A2. The second joint JT2 is configured by the second rotation shaft R2 and the bearing 51, whereby the second link 23 can freely rotate around the second rotation axis A2 with respect to the first link 22.

The second rotation shaft R2 is provided with a driven pulley 33. Meanwhile, the first link 22 is provided with a second motor M2 such that a central axis of a main shaft S2 is parallel to the second rotation axis A2. The second motor M2 is provided with a second rotation angle sensor E2 that detects a rotation angle of the second motor M2. The second rotation angle sensor E2 only needs to be able to detect the rotation angle, and is configured by, for example, an encoder or a tachometer. Here, the second rotation angle sensor E2 is configured by an encoder directly connected to the main shaft S2 of the second motor M2.

The main shaft S2 of the second motor M2 is provided with a driving pulley 32. A belt 34 is wound around the driving pulley 32 and the driven pulley 33. Therefore, the rotation angle of the second motor M2 created by the rotation of the second link 23 can be detected by the second rotation angle sensor E2, and the second motor M2 can rotationally drive the second rotation shaft R2.

Further, a tension coil spring (auxiliary spring) SP1 is provided between an appropriate position (here, center) of the second link 23 and the first link 22. The tension coil spring SP1 is provided such that a central axis of the tension coil spring SP1 is orthogonal to the second rotation axis A2 and the third rotation axis A3. Further, the tension coil spring SP1 is designed such that a predetermined torque acts on the second rotation shaft R2 in a rotation direction of the second link 23 when the second link 23 rotates from the reference posture. This predetermined torque is set so as to cancel a part of a torque generated on the second rotation shaft R2 by a weight of a part of the arm unit 11 from the second link 23 ahead and a weight of the wrist unit 12 (hereinafter, the torque may be referred to as a gravity torque). As a result, the part of the gravity torque generated on the second rotation shaft R2 is canceled by the tension coil spring SP1.

The third link 24 is formed in a rod-shaped box, and houses main elements therein. A third rotation shaft R3 is provided at the one end (rear end) of the third link 24. The third rotation shaft R3 is attached to the other end of the second link 23 via a bearing 52 rotatably around the third rotation axis A3. The third joint JT3 is configured by the third rotation shaft R3 and the bearing 52, whereby the third link 24 can freely rotate around the third rotation axis A3 with respect to the second link 23.

Meanwhile, the swing member 25 is formed in an elongated plate shape, and an eleventh rotation shaft R11 is provided at one end of the swing member 25. The eleventh rotation shaft R11 is attached to the other end of the first link 22 via a bearing 53 rotatably around the second rotation axis A2.

A ninth rotation shaft R9 is provided at the other end of the swing member 25. The ninth rotation shaft R9 is connected via a bearing (not shown) to the one end of the auxiliary link 26 rotatably around the ninth rotation axis A9.

Further, a tenth rotation shaft R10 is provided at a part between the one end of the third link 24 and the third joint JT3. The tenth rotation shaft is connected via a bearing (not shown) to the other end of the auxiliary link 26 rotatably around the tenth rotation axis A10. As described above, the auxiliary link 26 and the second link 23 configure parallel links.

Further, the eleventh rotation shaft R11 is provided with a driven pulley 44. Meanwhile, a third motor M3 is provided at an appropriate position of the first link 22 such that a central axis of a main shaft S3 is parallel to an eleventh rotation axis A11. The third motor M3 is provided with a third rotation angle sensor E3 that detects a rotation angle of the third motor M3. The third rotation angle sensor E3 only needs to be able to detect the rotation angle, and is configured by, for example, an encoder or a tachometer. Here, the third rotation angle sensor E3 is configured by an encoder directly connected to the main shaft S3 of the third motor M3.

The main shaft S3 of the third motor M3 is provided with a driving pulley 42. A belt 34 is wound around the driving pulley 42 and the driven pulley 33.

With the above configuration related to the auxiliary link 26, when the third link 24 rotates, the auxiliary link 26 moves in parallel to the second link 23, whereby the swing member 25 swings, and the driven pulley 44, the driving pulley 42, and the third motor M3 rotate in that order in accordance with the swing of the member 25. Therefore, by this series of operations, the rotation angle of the third motor M3 created by the rotation of the third link 24 can be detected by the second rotation angle sensor E2. Further, the third motor M3 can rotatably drive the third rotation shaft R3 by an operation reverse to this series of operations.

Further, a compression coil spring (not shown) is provided between the swing member 25 and the first link 22. The compression coil spring is designed to always generate a torque that rotates the swing member downward. This torque is set so as to cancel a part of the gravity torque generated on the ninth rotation shaft R9 by a weight of the third link 24 of the arm unit 11 and the weight of the wrist unit 12. Thus, part of the gravity torque generated on the ninth rotation shaft R9 is canceled by the coil spring.

{Wrist Unit 12}

Figure 6:
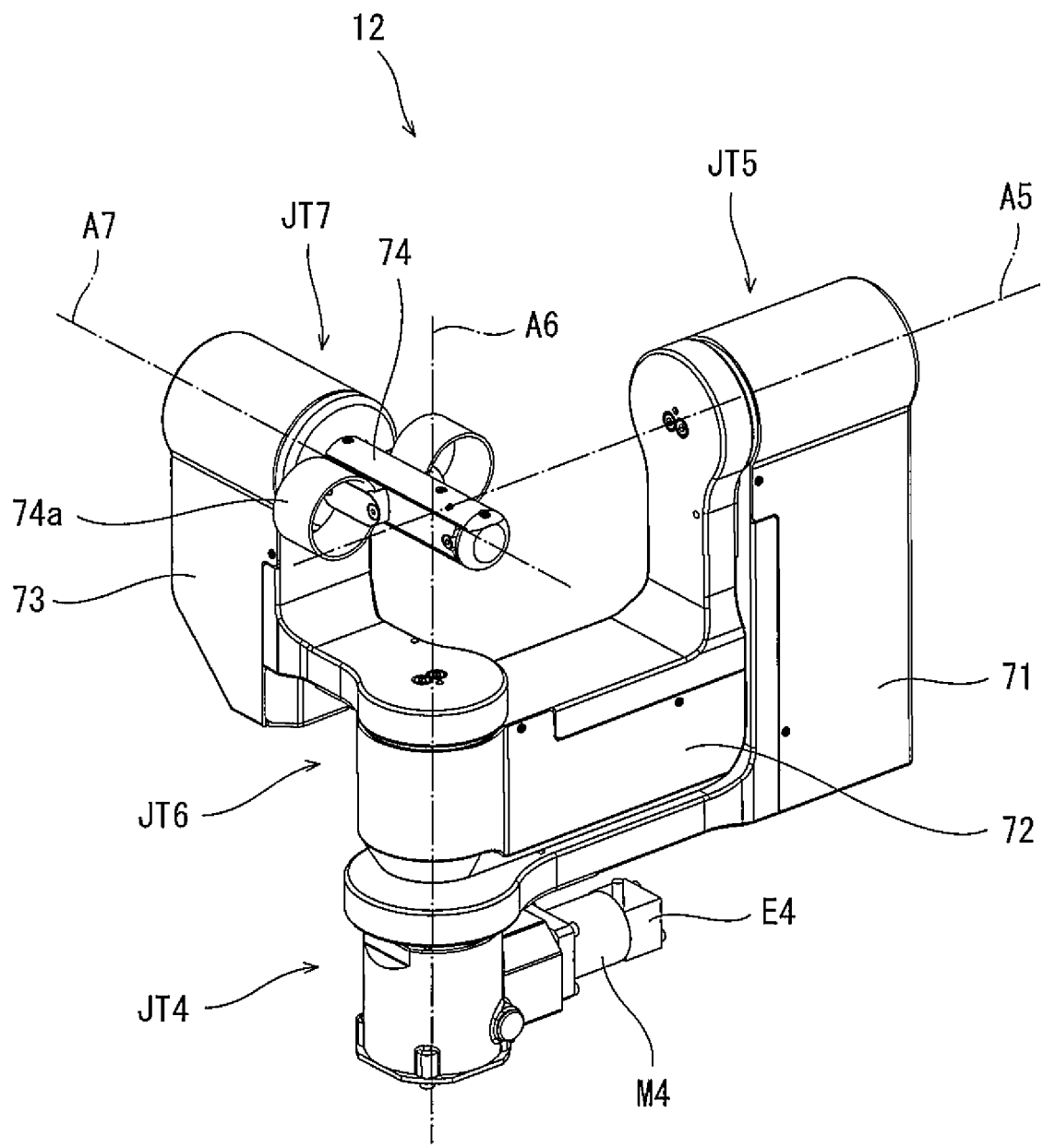
FIG. 6 is a perspective view showing an appearance of a wrist unit of the input device in FIG. 3.

FIG. 6 is a perspective view showing an appearance of the wrist unit 12 of the input device in FIG. 3. FIG. 6 shows the wrist unit 12 in the reference posture. Referring to FIG. 6, the wrist unit 12 includes, for example, a fourth link 71, a fifth link 72, a sixth link 73, and an operation unit 74 as a seventh link. The fourth link 71, the fifth link 72, the sixth link 73, and the operation unit 74 configure a three-axis (three degrees of freedom) gimbal. Specifically, the fifth link 72 is rotatable around a fifth rotation axis A5 with respect to the fourth link 71. The sixth link 73 is rotatable around a sixth rotation axis A6 orthogonal to the fifth rotation axis A5 with respect to the fifth link 72. The operation unit 74 is rotatable around a seventh rotation axis A7 orthogonal to the fifth rotation axis A5 and the sixth rotation axis A6 with respect to the sixth link 73. Therefore, the operator can rotate the operation unit 74 around an intersection of these three rotation axes A5 to A7 as a center to direct the operation unit 74 in any direction.

Referring to FIGS. 3 and 6, the fourth link 71 is formed in an L shape, and one end (front end in the reference posture) of the fourth link 71 is connected via the fourth joint JT4 to the other end (front end in the reference posture) of the third link 24 (see FIG. 3) rotatably around the fourth rotation axis. The fourth rotation axis A4 is orthogonal to the plane including the third rotation axis A3 and the tenth rotation axis A10.

Referring to FIG. 6, one end (rear end in the reference posture) of the fifth link 72 is connected via a fifth joint JT5 to the other end (rear end in the reference posture) of the fourth link 71 rotatably around the fifth rotation axis A5 orthogonal to the fourth rotation axis A4. The fifth link 72 is formed in an L shape slightly smaller than the fourth link 71. One end (right end in the reference posture) of the sixth link 73 is connected via a sixth joint JT6 to the other end (front end in the reference posture) of the fifth link 72 rotatably around the sixth rotation axis A6. The sixth link 73 is formed in an L shape slightly smaller than the fifth link 72. One end (left end in the reference posture) of the operation unit 74 is connected via a seventh joint JT7 to the other end (left end in the reference posture) of the sixth link 73 rotatably around the seventh rotation axis A7. The operation unit 74 includes a rod-shaped body and a pair of cylindrical finger insertion parts 74a provided on the body. The pair of finger insertion parts 74a is configured such that the operator can insert the thumb and the forefinger therein and operate the pair of finger insertion parts 74a as if pinching or releasing an object with the thumb and the forefinger.

Next, an example of a detailed structure of the wrist unit 12 will be described.

Figure 7:
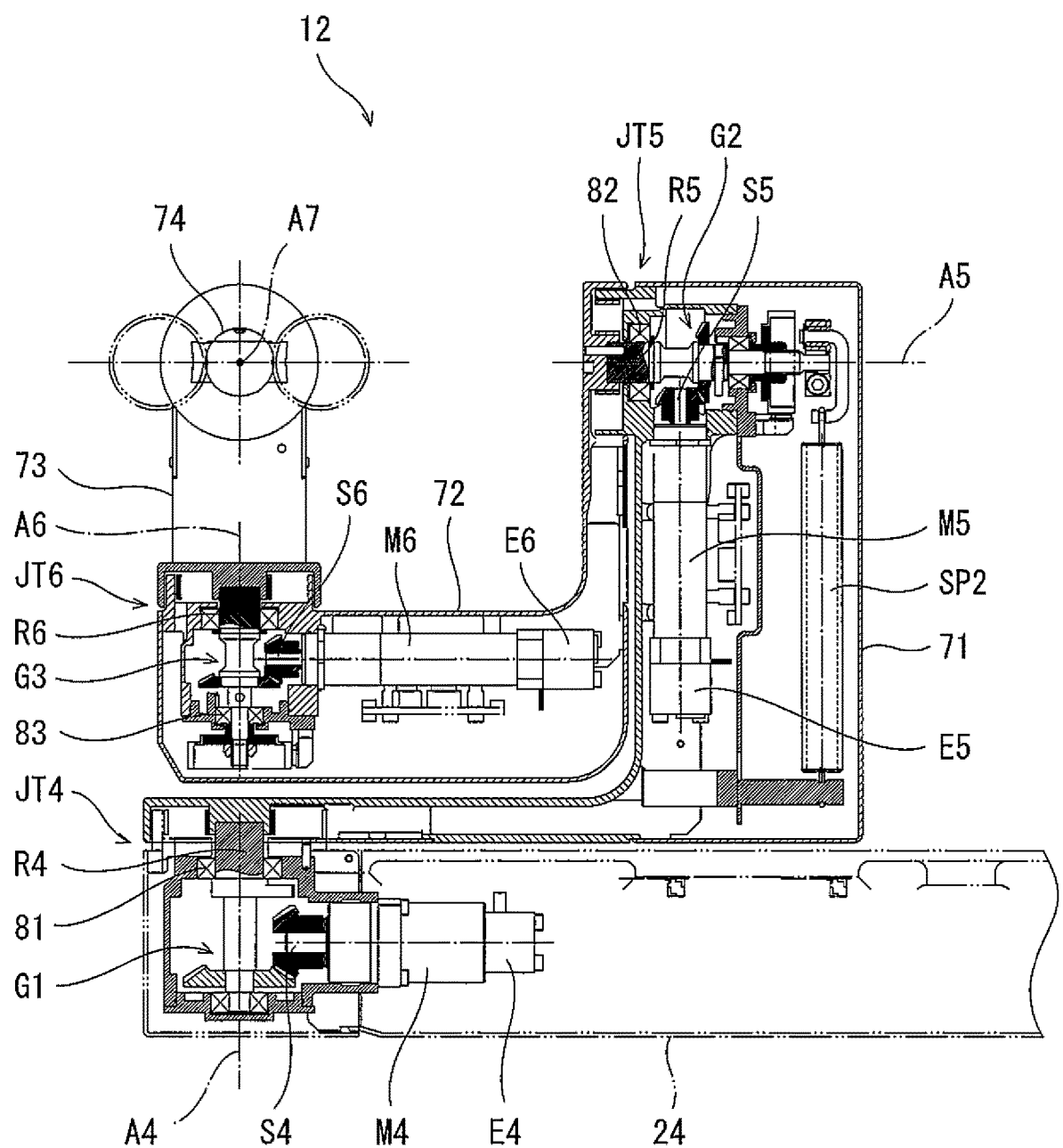
FIG. 7 is a cross-sectional view showing a vertical cross section of a fourth link and a fifth link of the wrist unit in FIG. 6.
Figure 8:
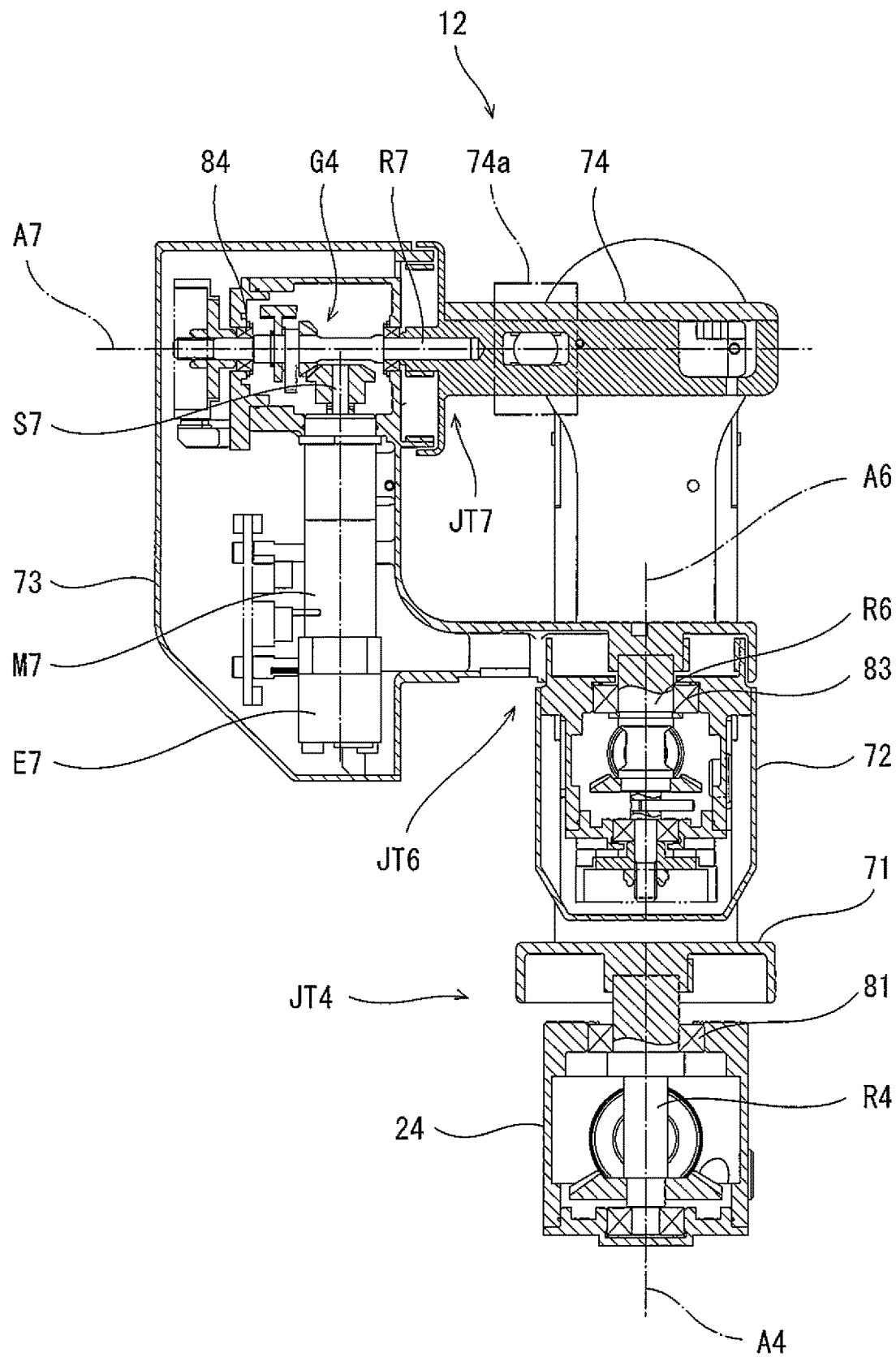
FIG. 8 is a cross-sectional view showing a vertical cross section of a sixth link and an operation unit of the wrist unit in FIG. 6.

FIG. 7 is a cross-sectional view showing a vertical cross section of the fourth link 71 and the fifth link 72 of the wrist unit 12 in FIG. 6. FIG. 8 is a cross-sectional view showing a vertical cross section of the sixth link 73 and the operation unit 74 of the wrist unit 12 in FIG. 6. FIG. 7 shows a cross section of the wrist unit 12 cut by a plane including the fifth rotation axis A5 and the sixth rotation axis A6. FIG. 8 shows a cross section of the wrist unit 12 cut by a plane including the sixth rotation axis A6 and the seventh rotation axis A7.

Referring to FIG. 7, the fourth link 71 is formed in an L-shaped box, and houses main elements therein. A fourth rotation shaft R4 is provided at the one end (front end) of the fourth link 71. The fourth rotation shaft R4 is attached to the other end (front end) of the third link 24 via a bearing 81 rotatably around the fourth rotation axis A4. The fourth rotation shaft R4 and the bearing 81 configure the fourth joint JT4, whereby the fourth link 71 can freely rotate around the fourth rotation axis A4 with respect to the third link 24.

Further, a fourth motor M4 is provided inside the third link 24 such that a center axis of a main shaft S4 is orthogonal to the fourth rotation axis A4. The fourth motor M4 is provided with a fourth rotation angle sensor E4 that detects a rotation angle of the fourth motor M4. The fourth rotation angle sensor E4 only needs to be able to detect the rotation angle, and is configured by, for example, an encoder or a tachometer. Here, the fourth rotation angle sensor E4 is configured by an encoder directly connected to the main shaft S4 of the fourth motor M4. The main shaft S4 of the fourth motor M4 is connected to the fourth rotation shaft R4 via a bevel gear mechanism G1. Therefore, the rotation angle of the fourth motor M4 created by the rotation of the fourth link 71 can be detected by the fourth rotation angle sensor E4, and the fourth motor M4 can rotationally drive the fourth rotation shaft R4.

The fifth link 72 is formed in an L-shaped box, and houses main elements therein. A fifth rotation shaft R5 is provided at the one end (rear end) of the fifth link 72. The fifth rotation shaft R5 is attached to the other end (rear end) of the fourth link 71 via a bearing 82 rotatably around a fifth rotation axis A5. The fifth rotation shaft R5 and the bearing 82 configure the fifth joint JT5, whereby the fifth link 72 can freely rotate around the fifth rotation axis A5 with respect to the fourth link 71.

Further, a fifth motor M5 is provided inside the fourth link 71 such that a center axis of a main shaft S5 is orthogonal to the fifth rotation axis A5. The fifth motor M5 is provided with a fifth rotation angle sensor E5 that detects a rotation angle of the fifth motor M5. The fifth rotation angle sensor E5 only needs to be able to detect the rotation angle, and is configured by, for example, an encoder or a tachometer. Here, the fifth rotation angle sensor E5 is configured by an encoder directly connected to the main shaft S5 of the fifth motor M5. The main shaft S5 of the fifth motor M5 is connected to the fifth rotation shaft R5 via a bevel gear mechanism G2. Therefore, the rotation angle of the fifth motor M5 created by the rotation of the fifth link 72 can be detected by the fifth rotation angle sensor E5, and the fifth motor M5 can rotationally drive the fifth rotation shaft R5.

Further, a compression coil spring SP2 (auxiliary spring) is provided between an appropriate position of the fourth link 71 (here, the lower end of the rear end in the reference posture) and the fifth rotation shaft R5. The compression coil spring SP2 is provided such that a central axis of the compression coil spring SP2 is parallel to the fourth rotation axis A4 and orthogonal to the fifth rotation axis A5. Further, the compression coil spring SP2 is designed such that when the fifth link 72 rotates from the reference posture, a predetermined torque acts on the fifth link 72 in the rotation direction. This predetermined torque is set so as to cancel a part of the gravity torque generated on the fifth rotation shaft R5 by a weight of a part of the wrist unit 12 from the fifth link ahead. As a result, the part of the gravity torque generated on the fifth rotation shaft R5 is canceled by the compression coil spring SP2.

Referring to FIGS. 7 and 8, the sixth link 73 is formed in an L-shaped box, and houses main elements therein. A sixth rotation shaft R6 is provided at the one end (right end) of the sixth link 73. The sixth rotation shaft R6 is attached to the other end (front end) of the fifth link 72 via a bearing 83 rotatably around the sixth rotation axis A6. The sixth rotation shaft R6 and the bearing 83 configure the sixth joint JT6, whereby the sixth link 73 can freely rotate around the sixth rotation axis A6 with respect to the fifth link 72.

Further, a sixth motor M6 is provided inside the fifth link 72 such that a center axis of a main shaft S6 is orthogonal to the sixth rotation axis A6. The sixth motor M6 is provided with a sixth rotation angle sensor E6 that detects a rotation angle of the sixth motor M6. The sixth rotation angle sensor E6 only needs to be able to detect the rotation angle, and is configured by, for example, an encoder or a tachometer. Here, the sixth rotation angle sensor E6 is configured by an encoder directly connected to the main shaft S6 of the sixth motor M6. The main shaft S6 of the sixth motor M6 is connected to the sixth rotation shaft R6 via a bevel gear mechanism. Thus, the rotation angle of the sixth motor M6 created by the rotation of the sixth link 73 can be detected by the sixth rotation angle sensor E6, and the sixth motor M6 can rotationally drive the sixth rotation shaft R6.

<Reduction Ratio>

Referring to FIG. 8, a seventh rotation shaft R7 is provided at the one end (left end) of the operation unit 74. The seventh rotation shaft R7 is attached to the other end (left end) of the sixth link 73 via a bearing 84 rotatably around the seventh rotation axis A7. The seventh rotation shaft R7 and the bearing 84 configure the seventh joint JT7, whereby the operation unit 74 can freely rotate around the seventh rotation axis A7 with respect to the sixth link 73.

Further, a seventh motor M7 is provided inside the sixth link 73 such that a center axis of a main shaft S7 is orthogonal to the seventh rotation axis A7. The seventh motor M7 is provided with a seventh rotation angle sensor E7 that detects a rotation angle of the seventh motor M7. The seventh rotation angle sensor E7 only needs to be able to detect the rotation angle, and is configured by, for example, an encoder or a tachometer. Here, the seventh rotation angle sensor E7 is configured by an encoder directly connected to the main shaft S7 of the seventh motor M7. The main shaft S7 of the seventh motor M7 is connected to the seventh rotation shaft R7 via a bevel gear mechanism G4. Thus, the rotation angle of the seventh motor M7 created by the rotation of the operation unit 74 can be detected by the seventh rotation angle sensor E7, and the seventh motor M7 can rotationally drive the seventh rotation shaft R7.

In the input device 2 configured as described above, reduction ratios in power transmission paths from the first to seventh motors M1 to M7 to the first to seventh joints JT1 to JT7, respectively, are designed to be 0.5 or more and 30 or less.

Referring to FIG. 3 and FIG. 5, the power transmission path from the first motor M1 to the first joint JT1 is configured by the main shaft S1 of the first motor M1 and the first rotation shaft R1. The power transmission path from the second motor M2 to the second joint JT2 is configured by the main shaft S2 of the second motor M2, the driving pulley 32, the belt 34, the driven pulley 33, and the second rotation shaft R2. The power transmission path from the third motor M3 to the third joint JT3 is configured by the main shaft S3 of the third motor M3, the driving pulley 42, the belt 45, the driven pulley 44, the eleventh rotation shaft R11, the swing member 25, the ninth rotation shaft R9, the auxiliary link 26, the tenth rotation shaft R10, the third link 24, and the third rotation shaft R3.

Referring to FIG. 7, the power transmission path from the fourth motor M4 to the fourth joint JT4 is configured by the main shaft S4 of the fourth motor M4, a bevel gear mechanism G1, and the fourth rotation shaft R4. The power transmission path from the fifth motor M5 to the fifth joint JT5 is configured by the main shaft S5 of the fifth motor M5, a bevel gear mechanism G2, and a fifth rotation shaft R5. The power transmission path from the sixth motor M6 to the sixth joint JT6 is configured by the main shaft S6 of the sixth motor M6, a bevel gear mechanism G3, and the sixth rotation shaft R6. Referring to FIG. 8, the power transmission path from the seventh motor M7 to the seventh joint JT7 is configured by the main shaft S7 of the seventh motor M7, a bevel gear mechanism G4, and the seventh rotation shaft R7.

When the reduction ratio is 30 or less, the operator can move the input device 2 lightly. On the other hand, as the reduction ratio decreases, an operation distance of the operation unit 74 required to move the surgical manipulator 202 by a predetermined distance increases. However, when the reduction ratio is 0.5 or more, no problem occurs in this respect.

In the input device 2, the reduction ratio in the arm unit 11 is designed to be smaller than the reduction ratio in the wrist unit 12. In general, a drag due to friction of a speed reducer, such as a reduction gear, of the arm unit 11 is larger than a drag due to friction of a speed reducer, such as a reduction gear, of the wrist unit 12. Therefore, when the reduction ratio of the arm unit 11 is smaller than the reduction ratio of the wrist unit 12, the operator can move the input device 2 more lightly.

The reduction ratio in the arm unit 11 is preferably 1 or more and 2 or less. When the reduction ratio is designed in this way, the operator can move the input device 2 more lightly.

Further, the reduction ratio in the wrist unit 12 is preferably 20 or more and 30 or less. When the reduction ratio is designed in this way, the operator can move the input device 2 more lightly.

In the above configuration example, for example, the reduction ratios in the power transmission paths from the first to third motors M1 to M3 to the first to third joints JT1 to JT3, respectively, are 1. Further, for example, the reduction ratios in the power transmission paths from the fourth to seventh motors M4 to M7 to the fourth to seventh joints JT4 to JT7, respectively, are 28.

{Configuration of Control System}

Figure 9:
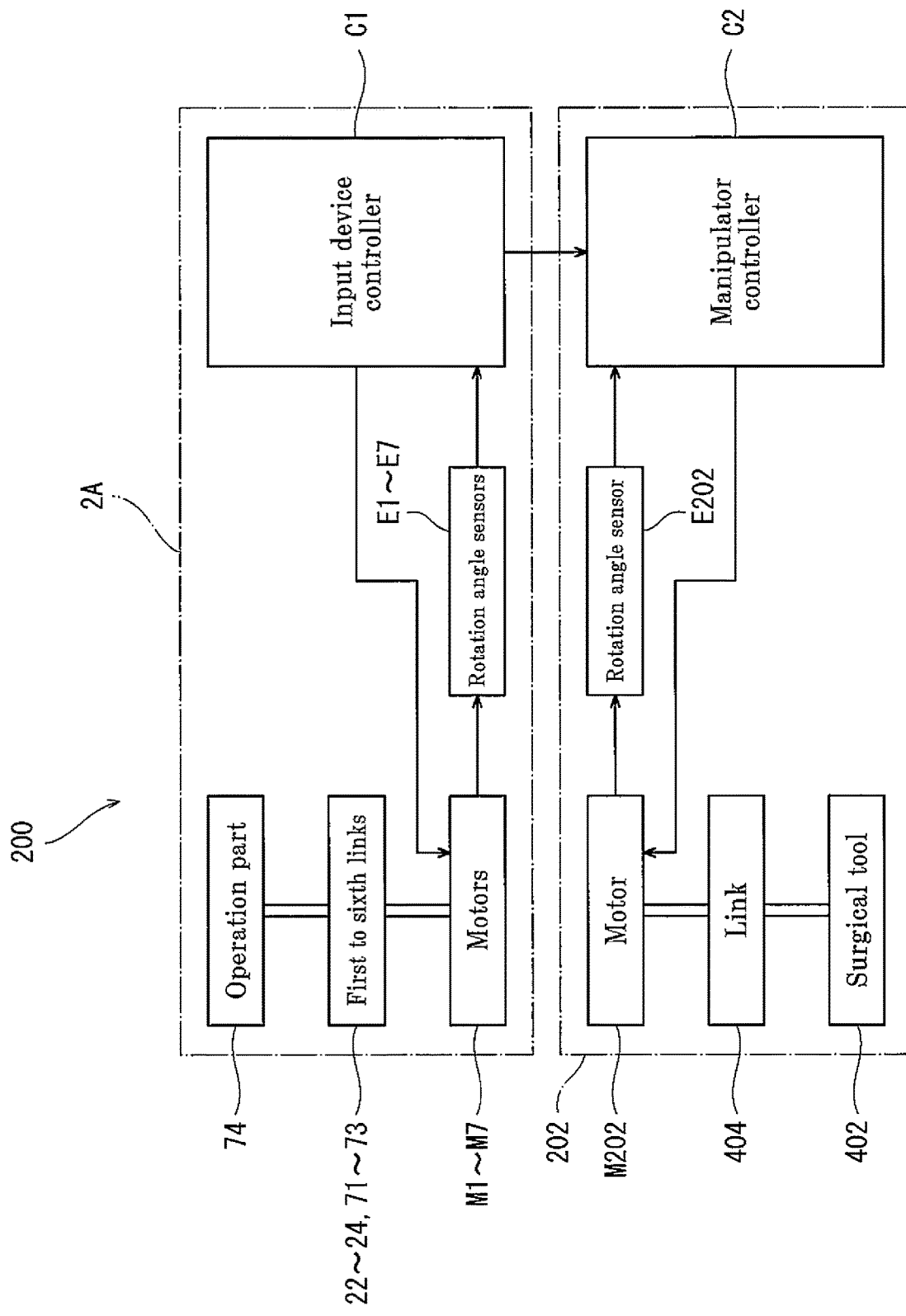
FIG. 9 is a functional block diagram showing an example of a configuration of a control system of the remote operation device and the surgical manipulator.

FIG. 9 is a functional block diagram showing an example of a configuration of a control system of the remote operation device 100 and the surgical manipulator 202.

Referring to FIG. 9, the remote operation device 100 includes an input device controller C1 that controls the right input device 2A. The input device controller C1 is, for example, provided commonly to the right input device 2A and the left input device 2B. Since the input device controller C1 controls both of the input devices similarly, here, only the control related to the right input device 2A will be described, and a description of the control related to the left input device 2B will be omitted. Note that an input device controller C1 may be provided to control the right input device 2A and the left input device 2B, individually. The input device controller C1 includes, for example, a control unit (not shown) and a servo amplifier (not shown). The control unit is configured by a single controller that performs centralized control or a plurality of controllers that performs distributed control. Here, the control unit is configured by a single controller that performs centralized control. The control unit includes, for example, a processor and a memory. The control unit controls an operation of the right input device 2A by causing the processor to read and execute a predetermined operation program stored in the memory. Specifically, the control unit includes, for example, a microcontroller, an MPU, a field programmable gate array (FPGA), a programmable logic controller (PLC), or a logic circuit.

In the right input device 2A, the first to seventh rotation angle sensors E1 to E7 detect the rotation angles of the first to seventh motors M1 to M7 respectively corresponding to the first to seventh joints JT1 to JT7. The detected rotation angles of the first to seventh motors M1 to M7 are output to the input device controller C1. In the input device controller C1, the control unit calculates a position of the operation unit 74 based on the input rotation angles of the first to seventh motors M1 to M7, and outputs the calculated position of the operation unit 74 (position command signal) to a manipulator controller C2 of the surgical manipulator 202. Further, the control unit calculates a current command value based on the input rotation angles of the first to seventh motors M1 to M7 such that postures of the arm unit 11 and the wrist unit 12 do not change due to gravity, and outputs the current command value to the servo amplifier. The servo amplifier outputs a current corresponding to the input current command value to the first to seventh motors M1 to M7. The postures of the arm unit 11 and the wrist unit 12 are thereby controlled so as not to change due to gravity. At this time, the rotation angles detected by the first to seventh rotation angle sensors E1 to E7 are used to feedback-control the postures of the arm unit 11 and the wrist unit 12.

The manipulator controller C2 includes, for example, a control unit (not shown) and a servo amplifier (not shown). The control unit is configured by a single controller that performs centralized control or a plurality of controllers that performs distributed control. Here, the control unit is configured by a single controller that performs centralized control. The control unit includes, for example, a processor and a memory. The control unit controls the operation of the surgical manipulator 202 by causing the processor to read and execute a predetermined operation program stored in the memory. Specifically, the control unit includes, for example, a microcontroller, an MPU, a field programmable gate array (FPGA), a programmable logic controller (PLC), or a logic circuit.

In the surgical manipulator 202, one or more rotation angle sensors E202 detect rotation angles of one or more motors M202 respectively corresponding to one or more joints that connect the link 404 and the surgical tool 402, and output the one or more detected rotation angles of the motor M202 to the manipulator controller C2. In the manipulator controller C2, the control unit calculates a current command value of the one or more motor M202 based on the position of the operation unit 74 (position command signal) input from the input device controller C1 such that the surgical tool 402 is positioned at a position corresponding to the position of the operation unit 74, and outputs the calculated current command value to the servo amplifier. The servo amplifier outputs a current corresponding to the input current command value to one or more motors M202. An operation of the link 404 is thereby controlled such that the surgical tool 402 is positioned at a position corresponding to the position of the operation unit 74. At this time, the rotation angle detected by the one or more rotation angle sensors E202 is used to feedback-control the position of the surgical tool 402.

Note that the posture and operation of the operation unit 74 of the input device 2A are separately detected by an appropriate sensor (not shown), and are input to the manipulator controller C2 via the input device controller C1. The manipulator controller C2 controls the surgical tool 402 such that the surgical tool 402 takes a posture corresponding to the posture of the operation unit 74 of the input device 2A and performs an operation corresponding to the operation of the operation unit 74 of the input device 2A.

[Operation]

First, the operations of the right input device 2A and the surgical manipulator 202 will be described.

Referring to FIGS. 3 and 6, the operator inserts, for example, the thumb and the forefinger finger into the pair of finger insertion parts 74a of the operation unit 74 of the right input device 2A. Then, when the operator moves the operation unit 74 left and right, the arm unit 11 rotates left and right around the first rotation axis A1 of the first joint JT1. When the operator moves the operation unit 74 back and forth, the arm unit 11 rotates back and forth around the second rotation axis A2 of the second joint JT2. When the operator moves the operation unit 74 up and down, the arm unit 11 rotates up and down around the third rotation axis A3 of the third joint JT3. When the operator rotates the wrist unit 12 right and left, the wrist unit 12 rotates right and left around the fourth rotation axis A4 of the fourth joint JT4. When the operator operates the operation unit 74 to change a direction (posture) of the operation unit 74, the operation unit 74 moves (takes a posture) in a direction to be changed. Therefore, the operator can operate the input device 2A as intended.

When the operation unit 74 of the right input device 2A is operated, this operation is converted into the position command signal by the input device controller C1. The manipulator controller C2 controls the operation of a selected one of the arms 401 in accordance with this position command signal such that the surgical tool 402 of the selected arm 401 of the surgical manipulator 202 is positioned at a position corresponding to the operation unit 74. Thus, the selected arm 401 of the surgical manipulator 202 operates in accordance with the operation of the right input device 2A by the operator. The arm 401 is selected by operating the pedals 4 of the remote operation device 100. An operation of the left input device 2B is similar to this operation.

Figure 10:
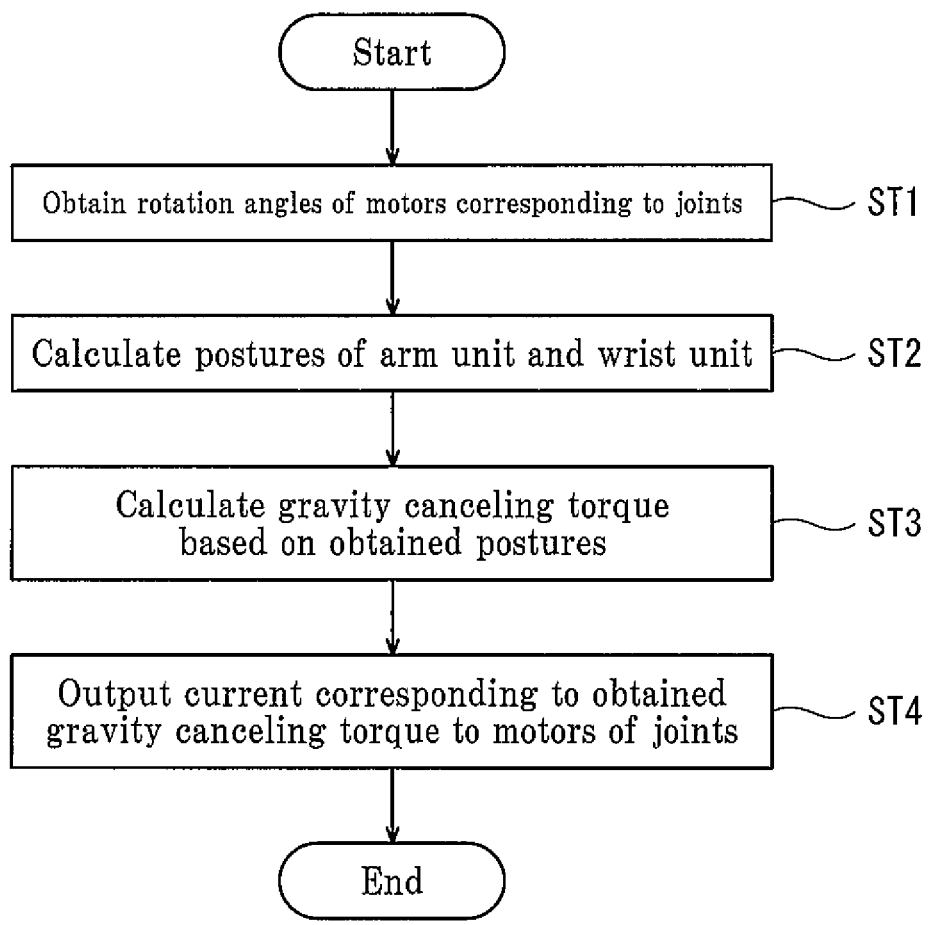
FIG. 10 is a flowchart showing an example of a gravity cancellation control of an input device controller in FIG. 9.

Next, a gravity cancellation control of the right input device 2A will be described. FIG. 10 is a flowchart showing an example of the gravity cancellation control of the input device controller C1 in FIG. 9.

Referring to FIG. 10, the control unit of the input device controller C1 performs the following control in real time based on control models of the arm unit 11 and the wrist unit 12.

First, the control unit of the input device controller C1 obtains the rotation angles of the motors M1 to M7 respectively corresponding to the joints JT1 to JT7 (step ST1).

Next, the control unit of the input device controller C1 calculates the postures of the arm unit 11 and the wrist unit 12 based on the obtained rotation angles of the motors M1 to M7 respectively corresponding to the joints JT1 to JT7 (step ST2).

Next, the control unit of the input device controller C1 calculates a gravity canceling torque that cancels the gravity torque generated on the rotation shafts R1 to R7 of the joints JT1 to JT7 based on the obtained postures (step ST3). Specifically, the control unit calculates the gravity torque determined for each of the rotation shafts R1 to R7 from the obtained postures. Then, in the joints JT2, JT3, and JT5 provided with the coil springs, the torque in the opposite direction to the torque obtained by subtracting the torque generated by the coil springs from the gravity torque is defined as the gravity canceling torque. In the joints JT1, JT4, JT6, and JT7 provided with no coil springs, the torque in the opposite direction to the gravity torque is defined as the gravity canceling torque.

Next, the servo amplifier of the input device controller C1 outputs a current corresponding to an obtained posture maintaining torque to the motors M1 to M7 respectively corresponding to the joints JT1 to JT7 (step ST4).

The gravity torque in the arm unit 11 and the wrist unit 12 is canceled, and thus the operator can operate the operation unit 74 of the right input device 2A without feeling the drag due to gravity. In addition, when the operator stops the operation of the operation unit 74, the operation unit 74 stops at a position where the operation is stopped, in a posture in which the operation is stopped.

As described above, in the input device 2 according to this embodiment, the input device controller C1 controls the operation of the plurality of motors M1 to M7 corresponding to the plurality of joints JT1 to JT7 such that the postures of the arm unit 11 and the wrist unit 12 do not change due to gravity. The operation unit 74 thereby stays at the position where the operator has stopped operating the operation unit 74, in the posture in which the operation is stopped.

Further, since the reduction ratios in the power transmission paths from the plurality of motors M1 to M7 to the plurality of joints JT1 to JT7, respectively, are 0.5 or more and 30 or less, the operator can move the input device 2 lightly.

Further, the predetermined joints JT2, JT3, and JT5 further include the auxiliary springs SP1 to SP3 that generate the torque that cancels a part of the torque generated in the predetermined joints JT2, JT3, and JT5 by the weight of the arm unit 11 or the wrist unit 12. This can reduce a load on the motors M2, M3, and M5 that drive the joints such that the postures of the arm unit 11 and the wrist unit 12 do not change due to gravity, and reduce the size of the motors M2, M3, and M5.

Other Embodiments

In Embodiment 1, the number of the joints of the arm unit 11 is three. However, it is sufficient that the number of the joints of the arm unit 11 is one or more.

In Embodiment 1, the wrist unit 12 has four joints, but the arm unit 11 may only require to have one or more joints.

In Embodiment 1, the reduction ratio in the arm unit is smaller than the reduction ratio in the wrist unit 12. However, the reduction ratio in the arm unit may be equal to or larger than the reduction ratio in the wrist unit 12.

In Embodiment 1, the third joint JT3 includes an auxiliary link mechanism (25, 26). However, the auxiliary link mechanism (25, 26) may be omitted.

In Embodiment 1, the second joint JT2, the third joint JT3, and the fifth joint JT5 are provided with the coil springs. However, the coil springs may be omitted. Further, all the joints may be provided with coil springs. Further, another urging device may be used instead of the coil springs.

From the above description, many modifications and other embodiments are apparent to a person skilled in the art. Therefore, the above description should be construed as illustrative only.

INDUSTRIAL APPLICABILITY

The input device for a surgical manipulator of the present invention is useful as an input device for a surgical manipulator that can be lightly moved by an operator.

REFERENCE SIGNS LIST 1 body
2 input device
2A right input device
2B left input device
3 support member
4 pedal
5 monitor
11 arm unit
12 wrist unit
21 base body
22 first link
23 second link
24 third link
25 swing member
26 auxiliary link
51 to 53 bearing
62 connection member
71 fourth link
72 fifth link
73 sixth link
74 operation unit
74a finger insertion part
81 to 84 bearing
100 remote operation device
200 robotically-assisted surgical system
201 positioner
202 surgical manipulator
203 operating table
204 patient
401 arm unit
402 surgical tool
404 link
A1 to A7 first to seventh rotation axes
A9 to A11 ninth to eleventh rotation axes
E1 to E7 first to seventh rotation angle sensors
G1 to G4 bevel gear mechanism
JT1 to JT7 first to seventh joints
M1 to M7 first to seventh motors
R1 to R7 first to seventh rotation shafts
R9 to R11 ninth to eleventh rotation shafts
S1 to S7 main shaft
SP1 tension coil spring
SP2 compression coil spring

The invention claimed is:

1. A remote operation device for a surgical manipulator, the remote operation device comprising an input device as a master input device that is configured to operate the surgical manipulator as a slave robot, wherein:
the input device includes:
an arm unit including a plurality of first joints and a plurality of first motors that are respectively configured to drive the plurality of first joints,
a wrist unit connected to a distal end of the arm unit and including a plurality of second joints and a plurality of second motors that are respectively configured to drive the plurality of second joints; and
an operation unit that is provided at a distal end of the wrist unit and is configured to be operated by an operator,
the arm unit includes a plurality of first speed reducers respectively arranged in first power transmission paths from the respective first motors to the respective first joints,
the wrist unit includes a plurality of second speed reducers respectively arranged in second power transmission paths from the respective second motors to the respective second joints,
first reduction ratios of the respective first speed reducers and second reduction ratios of the respective second speed reducers, respectively, are 0.5 or more and 30 or less, and
the first reduction ratios of the respective first speed reducers are smaller than the second reduction ratios of the respective second speed reducers.

2. The remote operation device according to claim 1, wherein the first reduction ratios of the respective first speed reducers are 1 or more and 2 or less.

3. The remote operation device according to claim 1, wherein the second reduction ratios of the respective second speed reducers are 20 or more and 30 or less.

4. The remote operation device according to claim 1, wherein the second reduction ratios of the respective second speed reducers are equal to or more than 10 times the first reduction ratios of the respective first speed reducers.

5. The remote operation device according to claim 1, wherein the arm unit includes three of the first joints, and the wrist unit includes three of the second joints.

6. The remote operation device according to claim 1, wherein the arm unit includes only three or four of the first joints, and the wrist unit includes only three of the second joints.

7. The remote operation device according to claim 6, wherein three joint axes of the three second joints of the wrist unit intersect at one point.

8. The remote operation device according to claim 1, further comprising a controller for controlling an operation of the first motors and the second motors, wherein:
the input device further includes:
a plurality of first rotation angle sensors for respectively detecting the rotation angles of the first motors or the rotation angles of the first joints, and
a plurality of second rotation angle sensors for respectively detecting the rotation angles of the second motors or the rotation angles of the second joints, and
the controller is configured to, based on the rotation angles detected by the first rotation angle sensors and the second rotation angle sensors,
i) calculate a position of the operation unit,
ii) output the calculated position of the operation unit to the surgical manipulator, and
iii) control the operations of the first motors and the second motors such that postures of the arm unit and the wrist unit do not change due to gravity.

9. The remote operation device according to claim 1, further comprising a controller for controlling an operation of the first motors and the second motors, wherein:
the input device further includes:
a plurality of first rotation angle sensors for respectively detecting the rotation angles of the first motors or the rotation angles of the first joints,
a plurality of second rotation angle sensors for respectively detecting the rotation angles of the second motors or the rotation angles of the second joints, and
an auxiliary spring that is provided in a predetermined joint of the first joints of the arm unit or the second joints of the wrist unit, and that is configured to generate a torque that cancels a part of a torque generated in the predetermined joint by a weight of the arm unit or the wrist unit, and
the controller is configured to control an operation of the first motors and the second motors based on the rotation angles detected by the first rotation angle sensors and the second rotation angle sensors and the torque generated by the auxiliary spring such that postures of the arm unit and the wrist unit do not change due to gravity.

10. A robotically-assisted surgical system comprising:
a surgical manipulator having a distal end to which a surgical tool is detachably attached,
a remote operation device including an input device as a master input device that is configured to operate the surgical manipulator as a slave robot, wherein:
the input device includes:
an arm unit including a plurality of first joints and a plurality of first motors that are respectively configured to drive the plurality of first joints,
a wrist unit connected to a distal end of the arm unit and including a plurality of second joints and a plurality of second motors that are respectively configured to drive the plurality of second joints; and
an operation unit that is provided at a distal end of the wrist unit and is configured to be operated by an operator,
the arm unit includes a plurality of first speed reducers respectively arranged in first power transmission paths from the respective first motors to the respective first joints,
the wrist unit includes a plurality of second speed reducers respectively arranged in second power transmission paths from the respective second motors to the respective second joints,
first reduction ratios of the respective first speed reducers and second reduction ratios of the respective second speed reducers, respectively, are 0.5 or more and 30 or less, and
the first reduction ratios of the respective first speed reducers are smaller than the second reduction ratios of the respective second speed reducers.

11. The robotically-assisted surgical system according to claim 10, further comprising a controller for controlling an operation of the surgical manipulator, wherein:
the input device includes:
a plurality of first rotation angle sensors for respectively detecting rotation angles of the first motors or rotation angles of the first joints, and
a plurality of second rotation angle sensors for respectively detecting rotation angles of the second motors or rotation angles of the second joints, and
the controller is configured to control the operation of the surgical manipulator based on the rotation angles detected by the first rotation angle sensors and the second rotation angle sensors.

12. The robotically-assisted surgical system according to claim 11,
wherein
the controller is configured to, based on the rotation angles detected by the first rotation angle sensors and the second rotation angle sensors,
i) calculate a position of the operation unit,
ii) output the calculated position of the operation unit to the surgical manipulator, and
iii) control the operations of the first motors and the second motors such that postures of the arm unit and the wrist unit do not change due to gravity.

13. The robotically-assisted surgical system according to claim 10, wherein the input device includes an auxiliary spring that is provided in a predetermined joint of the first joints of the arm unit or the second joints of the wrist unit, and that is configured to generate a torque that cancels a part of a torque generated in the predetermined joint by a weight of the arm unit or the wrist unit.

14. The robotically-assisted surgical system according to claim 13, wherein:
the remote operation device includes a controller for controlling operations of the first motors and the second motors,
the input device includes:
a plurality of first rotation angle sensors for respectively detecting the rotation angles of the first motors or the rotation angles of the first joints, and a plurality of second rotation angle sensors for respectively detecting the rotation angles of the second motors or the rotation angles of the second joints, and the controller is configured to control the operations of the first motors and the second motors based on the rotation angles detected by the first rotation angle sensors and the second rotation angle sensors and the torque generated by the auxiliary spring such that postures of the arm unit and the wrist unit do not change due to gravity.

15. The robotically-assisted surgical system according to claim 10, wherein the first reduction ratios of the first speed reducers are 1 or more and 2 or less.

16. The robotically-assisted surgical system according to claim 10, wherein the second reduction ratios of the second speed reducers are 20 or more and 30 or less.

17. The robotically-assisted surgical system according to claim 10, wherein the second reduction ratios of the second speed reducers are equal to or more than 10 times the first reduction ratios of the first speed reducers.

18. The robotically-assisted surgical system according to claim 10, further comprising a second surgical manipulator having a distal end to which a second surgical tool is detachably attached, wherein:

the remote operation device includes a second input device that is configured to operate the second surgical manipulator, the second input device includes:

a second arm unit including a plurality of third joints and a plurality of third motors that are respectively configured to drive the plurality of third joints, a second wrist unit connected to a distal end of the second arm unit and including a plurality of fourth joints and a plurality of fourth motors that are respectively configured to drive the plurality of fourth joints; and a second operation unit provided at a distal end of the second wrist unit and configured to be operated by the operator, the second arm unit includes a plurality of third speed reducers respectively arranged in third power transmission paths from the respective third motors to the respective third joints, the second wrist unit includes a plurality of fourth speed reducers respectively arranged in fourth power transmission paths from the respective fourth motors to the respective fourth joints, third reduction ratios of the respective third speed reducers and fourth reduction ratios of the respective fourth speed reducers, respectively, are 0.5 or more and 30 or less, and the third reduction ratios of the respective third speed reducers are smaller than the fourth reduction ratios of the respective fourth speed reducers.

19. The robotically-assisted surgical system according to claim 18, wherein the third reduction ratios of the respective third speed reducers are 1 or more and 2 or less.

20. The robotically-assisted surgical system according to claim 18, wherein the fourth reduction ratios of the respective fourth speed reducers are 20 or more and 30 or less.

* * * * *